(12) United States Patent
Kim et al.

(10) Patent No.: US 11,859,144 B2
(45) Date of Patent: Jan. 2, 2024

(54) OPERATING GUIDE SYSTEM OF COAL GASIFICATION PLANT AND APPARATUS AND METHOD THEREFOR

(71) Applicants: DOOSAN ENERBILITY CO., LTD., Changwon (KR); KOREA WESTERN POWER CO., LTD, Chungcheongnam-do (KR)

(72) Inventors: Bong Keun Kim, Yongin-si (KR); Jeong Seok Yoo, Yongin-si (KR); Sung Hee Kim, Seosan-si (KR); Jong Ho Oh, Chungcheongnam-do (KR); Jun Seok Kim, Chungcheongnam-do (KR)

(73) Assignee: DOOSAN ENERBILITY CO., LTD., Changwon (KR)

( * ) Notice: Subject to any disclaimer, the term of this patent is extended or adjusted under 35 U.S.C. 154(b) by 407 days.

(21) Appl. No.: 15/931,583

(22) Filed: May 14, 2020

(65) Prior Publication Data

US 2020/0369971 A1  Nov. 26, 2020

(30) Foreign Application Priority Data

May 20, 2019  (KR) .................. 10-2019-0059059

(51) Int. Cl.
  *C10J 3/72* (2006.01)
  *G01N 33/22* (2006.01)
  *G05B 23/02* (2006.01)

(52) U.S. Cl.
  CPC ............ *C10J 3/723* (2013.01); *G01N 33/222* (2013.01); *G05B 23/0283* (2013.01); *C10J 2300/06* (2013.01)

(58) Field of Classification Search
  CPC ..... C10J 2300/06; C10J 3/723; G01N 33/222; G05B 13/024; G05B 13/044;
  (Continued)

(56) References Cited

U.S. PATENT DOCUMENTS 4,182,957 A * 1/1980 Forster .................. G01N 23/12
378/54
4,489,562 A * 12/1984 Snyder .................. F01K 23/101
60/664
(Continued)

FOREIGN PATENT DOCUMENTS

CN  107868678 A  4/2018
KR  10-1071453 B1  10/2011
(Continued)

OTHER PUBLICATIONS

DBpia, Oct. 1995, 222-231(10 pages) Journal of Energy Engineering 4(2), Oct. 1995, 222-231(10 pages).

*Primary Examiner* — Imran Akram
(74) *Attorney, Agent, or Firm* — Harvest IP Law, LLP

(57) ABSTRACT

An operating guide system of a plant utilizing coal gasification includes a performance analyzer for analyzing performance of the plant by analyzing gasifier performance and synthesis gas cooler performance during an operation of the plant; an operation guide generator for generating an operation guide indicating control values for the operation of the plant based on the performance analysis of the plant; an action guide generator for generating an action guide indicating control values for controlling the plant to prevent an abnormal situation predicted in the plant based on the performance analysis of the plant; and a fuel determiner for determining gasification suitability of an analysis target fuel selected by a user before the plant is started, the gasification suitability including basic suitability and suitability of slag behavior.

12 Claims, 7 Drawing Sheets

(58) Field of Classification Search
CPC ............ G05B 23/0272; G05B 23/0283; G05B 23/0294; Y02P 90/82
See application file for complete search history.

(56) References Cited

U.S. PATENT DOCUMENTS

| | | | | |
|---|---|---|---|---|
| 4,791,817 | A * | 12/1988 | Albertz | G01F 1/74 73/861.04 |
| 4,936,870 | A * | 6/1990 | Baumann | C10J 3/50 406/197 |
| 9,092,124 | B2 | 7/2015 | Amminudin et al. | |
| 2003/0177963 | A1* | 9/2003 | Maxwell | F23G 5/04 110/224 |
| 2010/0146856 | A1* | 6/2010 | Zamansky | C10J 3/466 48/77 |
| 2012/0023822 | A1* | 2/2012 | D'Agostini | C10J 3/723 48/197 R |
| 2012/0085028 | A1* | 4/2012 | Leininger | C10J 3/485 48/197 R |
| 2012/0167543 | A1* | 7/2012 | Iida | F23N 5/082 60/39.12 |
| 2013/0277615 | A1* | 10/2013 | Steele | B01J 19/0006 252/373 |
| 2014/0083078 | A1* | 3/2014 | Dinu | F02C 3/22 60/776 |
| 2014/0360098 | A1* | 12/2014 | Naphade | C10J 3/723 48/89 |
| 2017/0183585 | A1* | 6/2017 | Yoshida | C10K 1/024 |
| 2018/0142627 | A1* | 5/2018 | Harper | F02C 9/40 |
| 2019/0072331 | A1* | 3/2019 | Yamamoto | C10J 3/485 |

FOREIGN PATENT DOCUMENTS

| | | |
|---|---|---|
| KR | 10-2012-0002298 A | 1/2012 |
| KR | 10-1376717 B1 | 3/2014 |
| KR | 10-1445909 B1 | 10/2014 |
| KR | 10-1625026 B1 | 5/2016 |

* cited by examiner

OPERATING GUIDE SYSTEM OF COAL GASIFICATION PLANT AND APPARATUS AND METHOD THEREFOR

CROSS-REFERENCE TO RELATED APPLICATION

This application claims priority to Korean Patent Application No. 10-2019-0059059, filed on May 20, 2019, the disclosure of which is incorporated by reference herein in its entirety.

BACKGROUND

Field

Exemplary embodiments of the present disclosure relate to an operating guide technology of a plant, and more particularly, to an operating guide system of a coal gasification plant and apparatus and method therefor.

Description of the Related Art

Integrated gasification combined cycle (IGCC) technology relates to a combined power generation system which generates synthesis gas ($CO+H_2$) by reacting coal with oxygen and water vapor at high temperature and high pressure, and drives a gas turbine and a steam turbine by using the synthesis gas as fuel. IGCC technology utilizes a new concept power generation method which combines existing coal-fired power plant, chemical plant, and combined cycle power, and is in the spotlight as an eco-friendly clean power generation technology because efficiency is high and pollution emission is low as compared to the existing coal-fired power plant. However, in the case of the coal gasification combined power generation plant, the basic design for systemization has not been established in the case of performance diagnosis and operating guide technology.

SUMMARY

Aspects of one or more exemplary embodiments provide a system capable of providing an operating guide of a coal gasification plant and an apparatus and a method therefor.

According to an exemplary embodiment, an operating guide system of a coal gasification plant is provided. The operating guide system may include a performance analyzer for analyzing performance of the plant by analyzing gasifier performance and synthesis gas cooler performance during an operation of the plant; and an operation guide generator for generating an operation guide indicating control values for the operation of the plant based on the performance analysis of the plant.

The operating guide system may further include an action guide generator for generating an action guide indicating control values for controlling the plant to prevent an abnormal situation predicted in the plant based on the performance analysis of the plant.

The operating guide system may further include a fuel determiner for determining gasification suitability of an analysis target fuel selected by a user before the plant is started, the gasification suitability including basic suitability and suitability of slag behavior. The fuel determiner may be configured to determine the gasification suitability of the analysis target fuel by determining the basic suitability and the suitability of slag behavior based on whether the analysis target fuel satisfies a predetermined reference value of basic attributes and a predetermined reference value of slag attributes; to output the determined gasification suitability by classifying whether the analysis target fuel is coal which may be used without flux or mixed coal, coal which may be used when the flux is input, coal which requires the mixed coal, or coal which is not suitable for the gasification; to determine the gasification suitability based on a flux input ratio input by the user, when the analysis target fuel comprises coal and flux; and to determine the gasification suitability while increasing a mixing ratio of target coal at a predetermined ratio (10 wt %), when the primary coal and at least one target coal added to the primary coal are selected by the user.

The operating guide system may further include an operating condition deriver for deriving operating conditions when the fuel is selected, the derived operating conditions including upper limit and lower limit temperatures of slag and upper limit and lower limit temperatures of gasifier. The operating condition deriver may be configured to derive the slag temperature limits by analyzing the crystal phase and solid-liquid equilibrium temperature of slag of the selected fuel and to derive the gasifier temperature limits based on the derived slag temperature limits.

The operating guide system may further include a start guide generator configured to generate a start-up table comprising a supply fuel input amount and main control factor state values for each step of a start-up process comprising coal burner stages of start, ready, and load up, and a guide based on the starting of the plant; and to output the supply fuel input amount and the main control factor state values for each step of the start-up process, when the plant is started. The start guide generator is configured to generate the supply fuel input amount and the main control factor state values for each step of the start-up process in the reverse order of the start-up process based on the supply fuel input amount of 100% load.

According to another exemplary embodiment, an operating guide system of a coal gasification plant is provided. The operating guide system may include a fuel determiner for determining gasification suitability of a selected analysis target fuel when the analysis target fuel is selected, before a plant is started; an operation condition deriver for deriving operating conditions when the fuel is selected, the derived operating conditions including upper limit and lower limit temperatures of slag and upper limit and lower limit temperatures of gasifier; a start guide generator for generating a guide based on the starting of the plant; a performance analyzer for analyzing performance of the plant by analyzing gasifier performance and synthesis gas cooler performance during an operation of the plant; and an operation guide generator for generating an operation guide indicating control values for operating the plant based on the performance analysis of the plant.

The operating guide system may further include an action guide generator which provides an action guide indicating control values capable of controlling the plant so that a predicted abnormal situation is eliminated, when the occurrence of the abnormal situation is predicted in the plant based on the performance analysis.

The operating guide system may further include a stop guide generator which provides a stop guide indicating control values for each step of a plurality of steps which stop the plant, when a stop event occurs during the operation of the plant.

According to still another exemplary embodiment, an operating guide method of a coal gasification plant is provided. The operating guide method may include analyzing performance of the plant by analyzing gasifier performance and synthesis gas cooler performance during an operation of the plant; and generating an operation guide indicating control values for operating the plant based on the performance analysis of the plant.

The operating guide method may further include, after the plant performance analyzing, generating an action guide indicating control values for controlling the plant to prevent an abnormal situation predicted in the plant based on the performance analysis of the plant.

The operating guide method may further include, before the plant performance analyzing: determining, before the plant is started, gasification suitability of an analysis target fuel by determining basic suitability and suitability of slag behavior based on whether the analysis target fuel satisfies a predetermined reference value of basic attributes and a predetermined reference value of slag attributes when the analysis target fuel is selected; and outputting the determined gasification suitability by classifying whether the analysis target fuel is coal which may be used without flux or mixed coal, coal which may be used when the flux is input, coal which requires the mixed coal, or coal which is not suitable for the gasification. The gasification suitability determining may include determining gasification suitability based on a flux input ratio input by a user, when the analysis target fuel comprises coal and flux; or determining the gasification suitability while increasing a mixing ratio of target coal at a predetermined ratio, when the analysis target fuel comprises a primary coal selected by the user and at least one target coal added to the primary coal.

The operating guide method may further include, before the plant performance analyzing: deriving operating conditions comprising upper limit and lower limit temperatures of slag and upper limit and lower limit temperatures of gasifier based on the selected fuel, when fuel to be input to the plant is selected; generating a start-up table comprising supply fuel input amount and main control factor state values for each step of a start-up process comprising coal burner stages of start, ready, and load up, when the plant is started; and generating a start guide based on the starting of the plant by outputting the supply fuel input amount and the main control factor state values for each step of the start-up process based on the start-up table. The slag temperature limits may be derived by analyzing the crystal phase and solid-liquid equilibrium temperature of slag of the selected fuel, and the gasifier temperature limits may be derived based on the derived slag temperature limits. The supply fuel input amount and the main control factor state values of the start-up table may be generated for each step of the start-up process in the reverse order of the start-up process based on the supply fuel input amount of 100% load.

The operating guide method may further include, after the operation guide generating, generating a stop guide indicating control values for each step of a plurality of steps which stop the plant, when a stop event occurs during the operation of the plant.

In accordance with the aspect of the present disclosure, by providing the guide to the driver throughout each step of the gasification plant operation, it is possible to expect the rapid improvement in the plant operation rate.

BRIEF DESCRIPTION OF THE DRAWINGS

The above and other aspects will become more apparent from the following description of the exemplary embodiments with reference to the accompanying drawings, in which.

DETAILED DESCRIPTION

Various changes and various embodiments may be made in the present disclosure, such that specific embodiments are illustrated and described in detail in the detailed description. It should be understood, however, that it is not intended to limit the present disclosure to the particular disclosed forms, but includes all modifications, equivalents, and alternatives falling within the sprit and technical scope of the present disclosure.

The terminology used in the present disclosure is merely for the purpose of describing particular embodiments, and is not intended to limit the present disclosure. The singular forms may include plural forms, unless the phrases clearly indicate the opposite. In the present disclosure, it should be understood that the term "comprising", "having", or the like specifies the presence of the characteristic, integer, step, operation, component, part, or a combination thereof described in the specification, and does not exclude the presence or addition possibility of one or more other characteristics, integers, steps, operations, components, parts or combinations thereof in advance.

Figure 1:
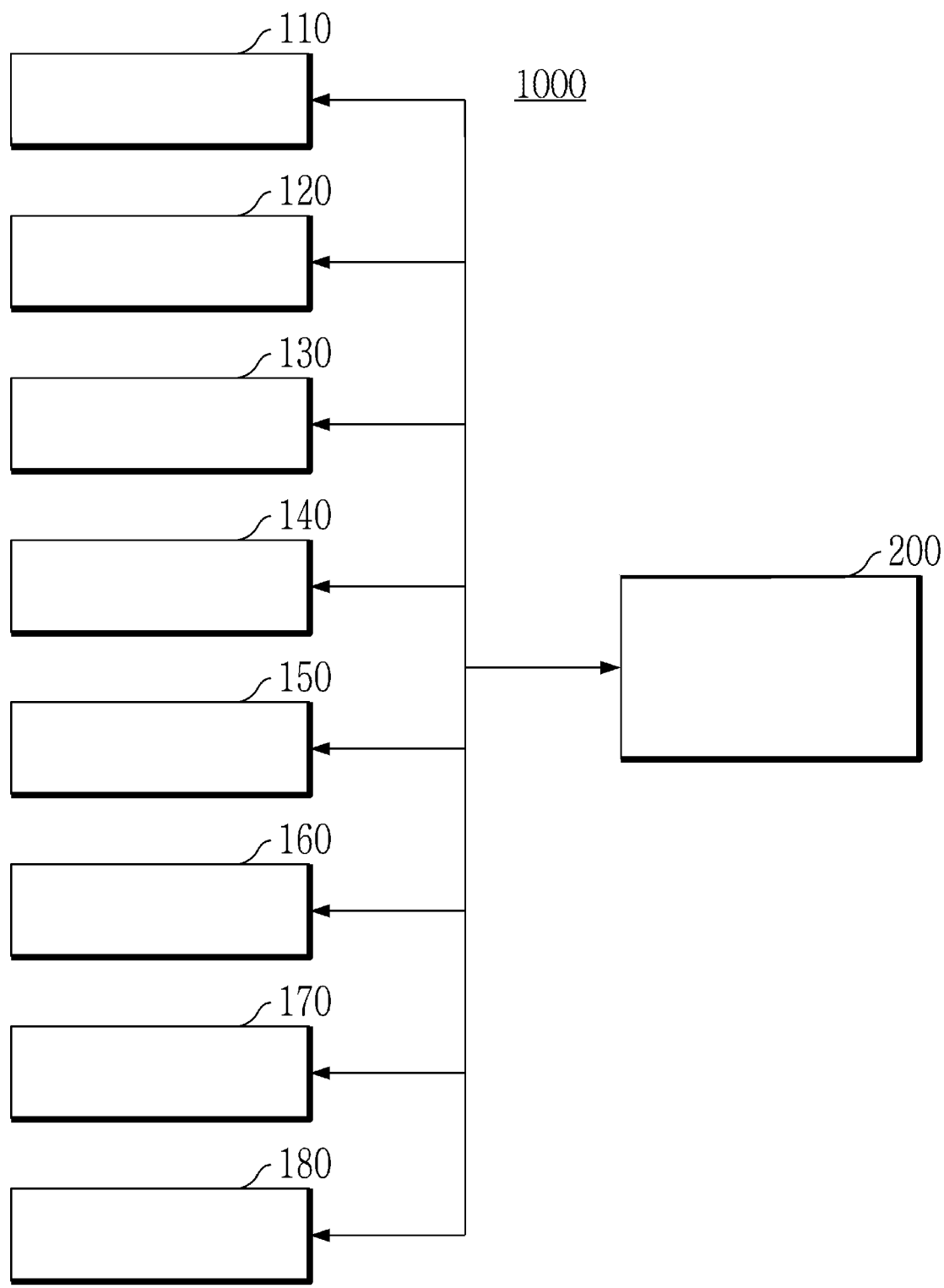
FIG. 1 is a block diagram of an operating guide system of a coal gasification plant according to an exemplary embodiment.

First, a configuration of an operating guide system 1000 of a coal gasification plant according to an exemplary embodiment will be described with reference to FIG. 1.

The operating guide system 100 includes a fuel determiner 110, an operating condition deriver 120, a start guide generator 130, a performance analyzer 140, an operation guide generator 150, an action guide generator 160, an operation recorder 170, a stop guide generator 180, and a storage 200.

The fuel determiner 110 determines gasification suitability of an analysis target fuel as selected by a user before the plant is started, where gasification suitability includes basic suitability and suitability of slag behavior. To do so, the fuel determiner 110 first determines the basic suitability and the suitability of slag behavior based on whether the analysis target fuel satisfies a predetermined reference value of the basic attributes and a predetermined reference value of the slag attributes. Here, the basic attributes may include coal heating amount (MJ/kg, MAF), volatile matter (wt %, MF), Cl+F (wt %, AR), $Fe_2O_3$ (wt %, ash), $Na_2O+K_2O$ (wt %, ash), S/A ratio (w/w, ash), and ash (wt %, ME); and the slag attributes may include coal conversion temperature (° C.), total slag thickness (mm), liquidus slag thickness (mm), average slag viscosity (poise), and muffle length versus slag thickness (%). In an exemplary embodiment, when the analysis target fuel contains coal and flux, the fuel determiner 110 may determine the gasification suitability based on a flux input ratio input by the user. In another exemplary embodiment, when the primary coal and at least one target coal added to the primary coal are selected by the user, the fuel determiner 110 determines the gasification suitability while increasing a mixing ratio of the target coal at a predetermined ratio (e.g., 10 wt %). Particularly, the fuel determiner 110 may output by classifying whether the analysis target fuel is coal which may be used without flux or mixed coal, coal which may be used when the flux is input, coal which requires the mixed coal, or coal which is not suitable for gasification based on the aforementioned determination results of the gasification suitability.

When the fuel is selected, the operating condition deriver 120 derives operating conditions. The derived operating conditions include upper limit and lower limit temperatures of the slag and upper limit and lower limit temperatures of the gasifier.

The operating condition deriver 120 derives the slag temperature limits by analyzing the crystal phase and the solid-liquid equilibrium temperature of the slag based on a composition ratio of components containing $SiO_2$, $Al_2O_3$, CaO, and FeO among the slag composition of the selected fuel, and derives the gasifier temperature limits based on the derived slag temperature limits.

The start guide generator 130 derives a start-up table including supply fuel input amount and main control factor state values for each step of the start-up process including coal burner stages of start, ready, and load up when the plant is started. At this time, the start guide generator 130 may derive the supply fuel input amount and the control factor state values for each step of the start-up process in the reverse order of the start-up process based on the supply fuel input amount of 100% load. In addition, the start guide generator 130 may provide a guide based on the starting of the plant by outputting the derived supply fuel input amount and control factor state values for each step of the start-up process.

The performance analyzer 140 basically performs the performance analysis of the plant including gasifier performance and synthesis gas cooler performance during the operation of the plant.

The operation guide generator 150 provides an operating guide indicating control values for operating the plant based on the performance analyzed by the performance analyzer 140.

When the occurrence of an abnormal situation is predicted in the plant based on the performance analysis, the action guide generator 160 provides an action guide indicating control values capable of controlling the plant so that the predicted abnormal situation is eliminated.

The operation recorder 170 may continuously store the control values based on the operation and action of the plant based on the user input, and provide the stored control values as the operating history.

When the stop event occurs during the operation of the plant, the stop guide generator 180 provides a stop guide indicating control values for each step of a plurality of steps which stop the plant.

The storage 200 stores various data as a database according to an exemplary embodiment.

Next, an operating guide method of the coal gasification plant according to an exemplary embodiment will be described with reference to FIG. 2.

Figure 2:
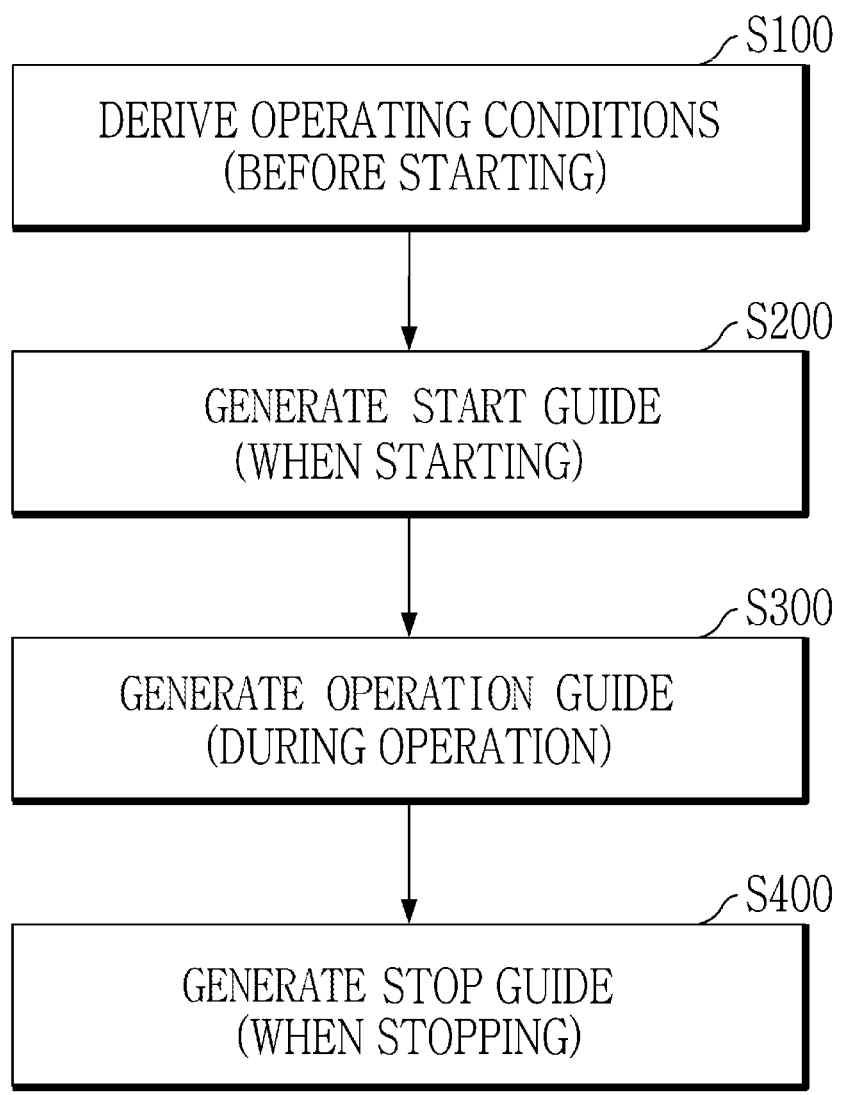
FIG. 2 is a flowchart of an operating guide method of the coal gasification plant according to an exemplary embodiment.

Referring to FIG. 2, the operating guide system determines fuels such as coal and mixed coal in S100 before the plant is started, and derives operating conditions after determining the gasification suitability for the determined fuel.

Next, the operating guide system derives a start-up table based on the operating conditions derived in S200 while the plant is started, and provides a guide based on the starting of the plant.

Subsequently, after the plant is started, the operating guide system analyzes the performance of the plant including the gasifier in S300 during operation, provides the guide necessary for the operation and control based on the analyzed performance, and provides the guide for the alarm and action by the occurrence of the abnormal situation or the like as necessary.

Meanwhile, the operating guide system provides the guide necessary for stopping the plant in S400, when the operation is stopped.

The step S100 of FIG. will be described with reference to FIG. 3.

Figure 3:
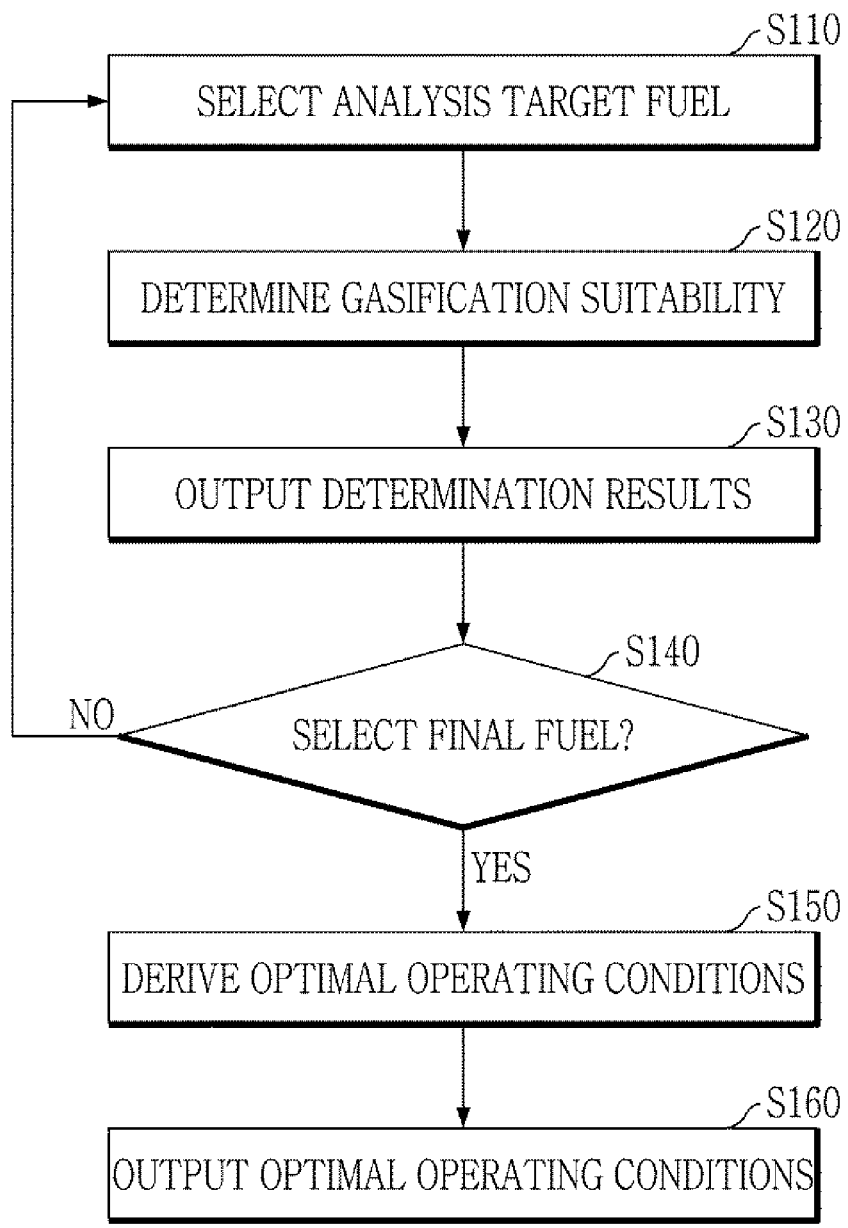
FIG. 3 is a flowchart of a method of determining gasification suitability for fuel and deriving operating conditions according to an exemplary embodiment.

Referring to FIG. 3, the fuel determiner 110 may select an analysis target fuel based on the user input in S110. At this time, the user may select a coal which may be used without flux or mixed coal, select coal and flux, or select mixed coal.

Next, the fuel determiner 110 determines the gasification suitability for the analysis target fuel selected by the user in S120. The gasification suitability includes basic suitability and suitability of slag behavior. That is, the fuel determiner 110 determines the basic suitability and the suitability of slag behavior of the analysis target fuel based on whether the analysis target fuel satisfies the predetermined reference value of basic attributes (physical properties) and the predetermined reference value of slag attributes in S120. The basic attributes include, for example, coal heating amount (MJ/kg, MAF), volatile matter (wt %, MF), Cl+F (wt %, AR), $Fe_2O_3$ (wt %, ash), $Na_2O+K_2O$ (wt %, ash), S/A ratio (w/w, ash), ash (wt %, MF), and the like. In addition, the slag attributes include, for example, coal conversion temperature (° C.), slag 250 viscosity (poise) temperature (° C.), total slag thickness (mm), liquidus slag thickness (mm), average slag viscosity (poise), muffle length versus slag thickness (%), and the like. At this time, when the user selects coal and flux, the fuel determiner 110 determines the basic suitability of the coal and the suitability of the slag behavior based on the flux input ratio input by the user. In addition, in the case of mixed coal, when the primary coal selected by the user and at least one target coal added to the primary coal are selected, the fuel determiner 110 may analyze the mixed coal while increasing the mixing ratio of the target coal at a predetermined ratio (e.g., 10 wt %).

Subsequently, the fuel determiner 110 outputs the determination results of the gasification suitability on a screen in S130. Here, the determination results of the fuel suitability based on the basic attributes and the slag attributes output by classifying whether it is fuel which may be used without flux or mixed coal, fuel which may be used when the flux is input, fuel which requires the mixed coal, or fuel which is not suitable for the gasification. For example, the determination results of the fuel suitability may be output by being classified as good, caution, or bad. Here, the good classification indicates that the analysis target fuel may be used for the corresponding plant, and the bad classification indicates that it is the fuel which is not suitable for the gasification. In addition, the caution classification indicates a state where the necessary flux input amount exceeds the flux input upper limit value of the corresponding plant or additional mixed coal is needed.

The user may finally select the fuel based on the determination results of the gasification suitability. Otherwise, the steps S110 to S130 of FIG. 3 are repeatedly performed. When the fuel is finally selected in S140, the step 100 proceeds to S150.

The operating condition deriver 120 derives the optimum operating conditions of the gasifier of the fuel selected in S150. The optimum operating conditions of the gasifier include slag temperature limits, gasifier upper limit, lower limit, and proper operating temperatures, operation window, ash addition input and circulation rate, flux input rate and the type (limestone or silica), and the like. At this time, the operating condition deriver 120 may derive the slag temperature limits by analyzing the crystal phase and the solid-liquid equilibrium temperature of the slag based on the composition ratio of the components containing $SiO_2$, $Al_2O_3$, CaO, and FeO among the slag composition of the selected fuel. In addition, the operating condition deriver 120 derives the upper limit, lower limit, and proper operating temperatures of the gasifier based on the slag temperature limits. Particularly, when operating the gasifier with the selected fuel, the operating condition deriver 120 may derive by analyzing that the slag mixed with the ash and flux of the fuel changes to liquidus slag at what temperature (° C.), and that the slag changes to what structure when the crystallization progresses to the solid. Accordingly, the operating condition deriver 120 may derive a change in the average viscosity of the liquidus flow slag based on the internal temperature of the gasifier, and derive the operation window of the gasifier for the selected fuel based on the above.

Then, the operating condition deriver 120 outputs the gasifier optimum operating conditions previously derived through the screen in S160.

The step S200 of FIG. 2 will be described with reference to FIG. 4.

Figure 4:
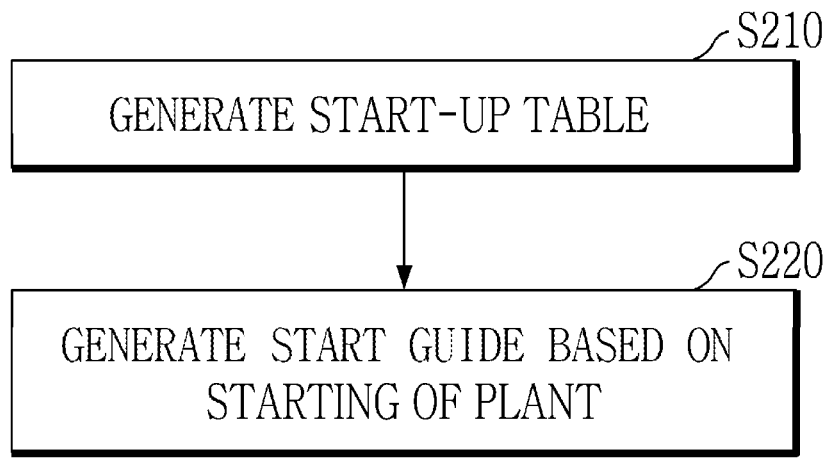
FIG. 4 is a flowchart of a method of generating a start guide necessary for starting the plant according to an exemplary embodiment.

Referring to FIG. 4, the start guide generator 130 generates a start-up table based on the gasifier optimum operating conditions of the selected fuel previously derived in S210. To start the plant, the start guide generator 130 performs the start-up process composed of three step which includes coal burner stages of start, ready, and load up. The start-up table includes the supply fuel input amount and main control factor state values for each step of the coal burner stage. Specifically, the start-up table includes 1) the flux type and flow rate ratio considering operating temperature and type of coal; 2) the optimum supply fuel flow rate considering operating temperature and capacity; 3) the gasifier and post facility performance; and 4) the optimal feedstock flow rate and control factor values based on each of step of the coal burner stages of the start-up process.

That is, the start guide generator 130 calculates the supply fuel flow rate and gasification performance necessary for each load-up step from starting the fuel and oxygen flow rate, which are necessary for operating a first coal burner, and gasification performance prediction values based on the previously derived gasifier optimum operating conditions of the selected fuel to the 100% operating load, and generates the start-up table based on the above.

The start guide generator 130 derives the supply fuel input amount and the control factor state values for each step of the coal burner stages of the start-up in the reverse order (i.e., load up, ready, and start) of the start-up process based on the supply fuel input amount of 100% load. That is, the start guide generator 130 first determines the optimum supply fuel input amount of the load for each step by reducing the input amount based on the optimum supply fuel input amount of the 100% load which is derived through the gasifier performance prediction. In addition, the start guide generator 130 determines the oxygen input amount of the load for each step by reducing the oxygen input amount in a simple proportional formula based on the oxygen input amount of the 100% load. In addition, the start guide generator 130 determines the operating temperature for each load to be equal to the operating temperature of the 100% load, and also determines the steam/$O_2$ ratio and the flux/coal ratio for each load to be equal to the ratio of the 100% load.

The start guide generator 130 provides the guide based on the starting of the plant by outputting the supply fuel input amount and the control factor state values for each step of the coal burner stages of the start-up based on the start-up table in S220.

Figure 5:
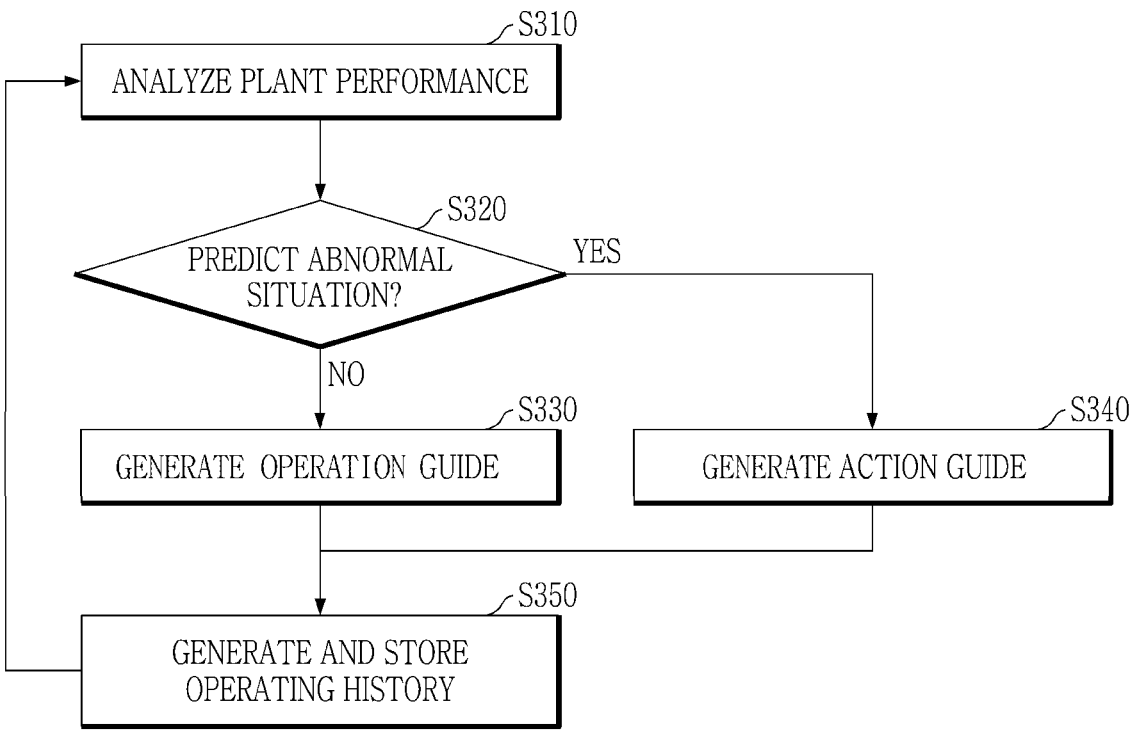
FIG. 5 is a flowchart of a method of generating an operation guide necessary for operating the plant according to an exemplary embodiment.

The step S300 will be described with reference to FIG. 5.

The plant (gasification plant) according to an exemplary embodiment produces the synthesis gas by gasifying coal. That is, coal, flux, oxygen, steam, and nitrogen for transport are supplied to four coal burners installed under the gasifier during the operation of the plant, thereby producing the synthesis gas through pyrolysis-combustion-gasification processes. In an exemplary embodiment, a control is needed to set the operation window and to adjust an $O_2$/coal ratio, steam/$O_2$ ratio, and the like so that during the operation of the plant, cold gas efficiency at which the coal energy is converted into the synthesis energy is increased, a carbon conversion rate is increased, and the molten slag is discharged smoothly.

To this end, the operation guide generator 150 analyzes the plant performance in real time during the operation of the plant in S310. The plant performance analysis includes gasifier performance analysis and synthesis gas cooler performance analysis.

The gasifier performance analysis includes gasification reaction analysis and internal heat transfer and heat balance analyses for the gasifier. The gasification reaction analysis uses an equilibrium reaction analysis model based on Gibbs energy minimization. At this time, the operation guide generator 150 determines the fraction set of the product in which the total Gibbs energy becomes a minimum at given temperature and pressure conditions based on the product in the gasification reaction analysis. The set of the product includes {CO, $CO_2$, $H_2$, $H_2O$, $H_2S$, COS, $NH_3$, HCl, $CH_4$, HCN, $N_2$, Ar, C, S, Cl, $O_2$} and calculates a total of sixteen types of product concentrations. The operation guide generator 150 calculates the heat input to the gasifier, the output heat, and the lost heat through the gasifier heat balance and heat transfer analyses.

The synthesis gas cooler performance analysis includes outlet temperature prediction together with the synthesis gas cooler performance analysis. The operation guide generator 150 calculates synthesis gas temperature and Heat Duty for each heat exchange section of the synthesis gas cooler through the synthesis gas cooler performance analysis.

In S320, it is determined whether the occurrence of an abnormal situation is predicted based on the plant performance analysis result. As the determination result in the S320, when the occurrence of the abnormal situation is not predicted, the step S300 proceeds to S330, and when the occurrence of the abnormal situation is predicted, the step S300 proceeds to S340.

When the occurrence of the abnormal situation is not predicted, the operation guide generator 150 provides the operating guide based on the plant performance analysis in S330. The operating guide indicates control values capable of operating the plant so that cold gas efficiency of the plant is increased, a carbon conversion rate is increased, and the molten slag is discharged smoothly based on the real-time plant performance analysis. The operating control values indicate the supply amounts and operating temperatures of coal, flux, oxygen, steam, and nitrogen for transport.

When the occurrence of the abnormal situation is predicted, the action guide generator 160 provides the action guide indicating the necessary action in response to the predicted abnormal situation in S340. The action guide indicates action control values which allow the abnormal situation to be eliminated, and the action control values include the supply amounts and operating temperatures of the coal, flux, oxygen, steam, and nitrogen for transport. Accordingly, the user may operate the plant based on the operating guide or the action guide.

Meanwhile, the operation recorder 170 continuously stores the control values based on the operation and action of the plant based on the user input, and provides the stored control values as the operation history in S350.

Figure 6:
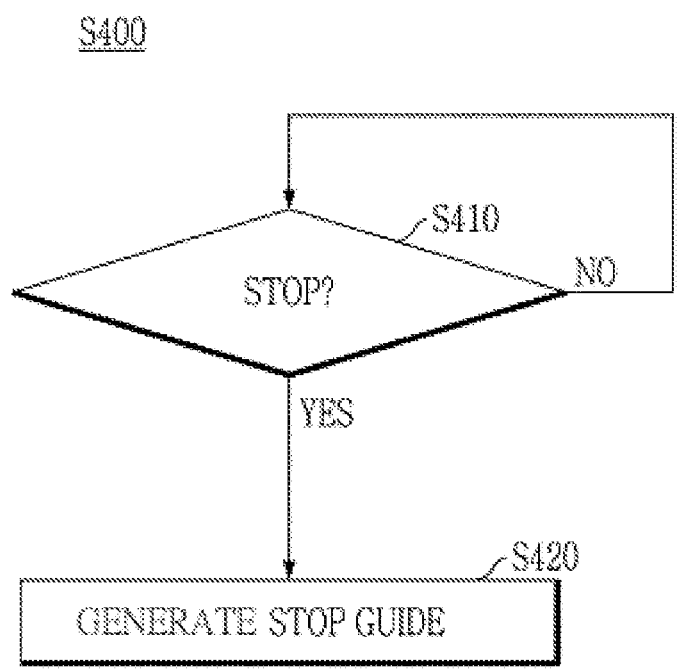
FIG. 6 is a flowchart of a method of generating a stop guide for stopping the plant according to an exemplary embodiment.

The step S400 of FIG. 2 will be described with reference to FIG. 6.

The stop guide generator 170 determines whether a plant stop event occurs in S410. The plant stop event may be an automatic stop based on an emergency situation or made by the user input.

When the stop event occurs, the stop guide generator 170 provides a stop guide for stopping the plant in S420. The stop guide includes control values inevitably controlled by the user for each step of a plurality of steps which stop the plant.

Figure 7:
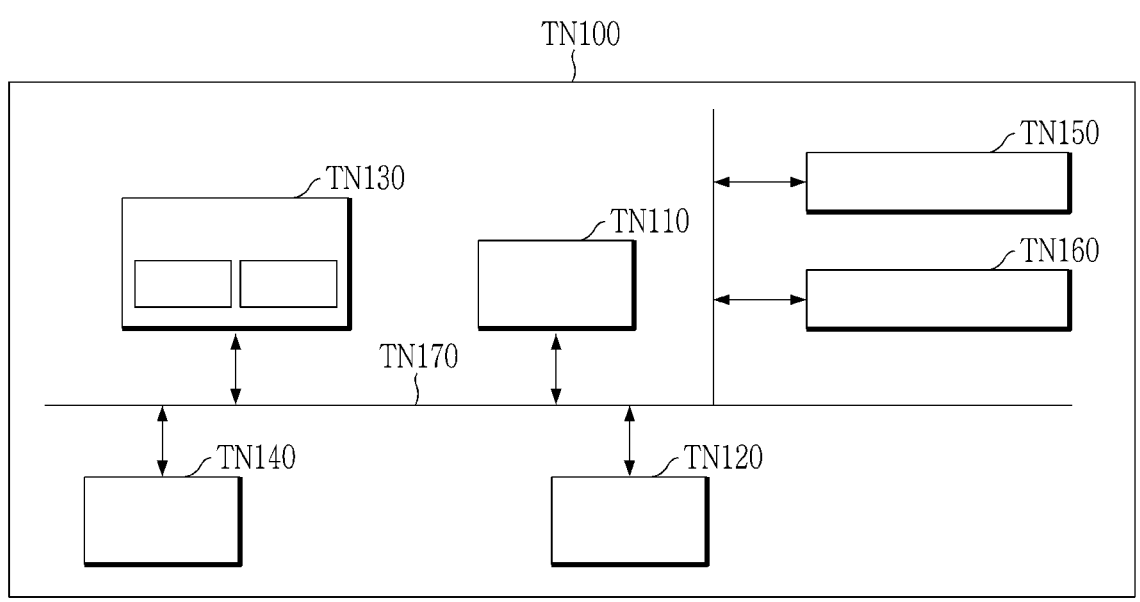
FIG. 7 is a block diagram of a computing apparatus according to an exemplary embodiment.

FIG. 7 illustrates a computing apparatus TN100 according to an exemplary embodiment. The operating guide system 1000 of the coal gasification plant may employ the computing apparatus TN100 of FIG. 7 to execute the method of FIG. 2.

In an exemplary embodiment of FIG. 7, the computing apparatus TN100 may include at least one processor TN110, a transceiver TN120, and a memory TN130. The computing apparatus TN100 may further include a storage device TN140, an input interface device TN150, an output interface device TN160, and the like. The components included in the computing apparatus TN100 may be connected by a bus TN170 to communicate with each other.

The processor TN110 may execute a program command stored in at least one of the memory TN130 and the storage device TN140. The processor TN110 may include one or more of a central processing unit (CPU), a graphics processing unit (GPU), and a dedicated processor to execute methods according to an exemplary embodiment. The processor TN110 may be configured to implement the procedure, function, method, and the like described in connection with exemplary embodiments. The processor TN110 may control each component of the computing apparatus TN100.

Each of the memory TN130 and the storage device TN140 may store various information related to an operation of the processor TN110. Each of the memory TN130 and the storage device TN140 may include at least one of a volatile storage medium and a nonvolatile storage medium, and the memory TN130 may include at least one of a read only memory (ROM) and a random access memory (RAM).

The transceiver TN120 may transmit and receive a wired signal or a wireless signal. The transceiver TN120 may be connected to a network to perform communication.

Meanwhile, the methods according to the aforementioned exemplary embodiment may be implemented in a program form readable through computer means to be recorded on a computer-readable recording medium. Here, the recording medium may include program commands, data files, data structures, and the like alone or in combination. The program commands recorded on the recording medium may be those specially designed and configured for the present disclosure or may also be known and available to those skilled in computer software. For example, the recording medium may be magnetic media such as hard disks, floppy disks, and magnetic tapes; optical media such as CD-ROMs and DVDs; magnetic-optical media such as floptical disks; and hardware devices specifically configured to store and perform the program commands, such as ROMs, RAMs, and flash memories. Examples of the program commands may include high-level language wiring executable by a computer using an interpreter, as well as machine language wiring such as those produced by a compiler. Such hardware devices may be configured to operate as one or more software modules to perform the operations of the present disclosure, and vice versa.

As described above, although an exemplary embodiment has been described, those skilled in the art may modify and change variously by adding, changing, deleting, or the like the components without departing from the spirit of the present disclosure described in the claims, and this will also be included within the scope of the present disclosure.

What is claimed is:

1. An operating guide system of a plant utilizing coal gasification, the operating guide system comprising:
   an input interface;
   a screen;
   a processor; and
   a storage, connected with the processor by a bus, storing one or more programs configured to be executed by the processor, the one or more programs including instructions for:
   receiving, by the input interface, an input selecting a fuel having basic attributes information and slag attributes information;
   determining, before the plant is started, gasification suitability type information of the selected fuel, based on a first comparison between the basic attributes information of the selected fuel and a first predetermined reference value and a second comparison between the slag attributes information of the selected fuel and a second predetermined reference value;
   storing the gasification suitability type information;
   generating performance analysis information of the plant by analyzing, while the plant is operated using the selected fuel, gasifier performance information and synthesis gas cooler performance information of the plant;
   generating an operation guide information indicating operation control values for the operation of the plant based on the generated performance analysis of the plant; and
   displaying, on the screen, the operation guide information with the operation control values,
   wherein the basic attributes information includes coal heating amount (MJ/kg, MAF), volatile matter (wt %, MF), Cl+F (wt %, AR), $Fe_2O_3$ (wt %, ash), $Na_2O+K_2O$ (wt %, ash), S/A ratio (w/w, ash), and ash (wt %, MF) of the selected fuel.

2. The operating guide system of claim 1, wherein the one or more programs further include instruction for:
   generating an action guide information providing abnormality prevention control values for controlling the plant which are used in preventing an abnormal operation predicted in the plant based on the performance analysis information of the plant.

3. The operating guide system of claim 1, wherein the determining gasification suitability type information comprising:
outputting the determined gasification suitability type information by classifying the selected fuel into one of a plurality of fuel types, the plurality fuel types including a first fuel type being a coal which may be used without being added with flux or another coal, a second fuel type being a coal which may be used when the flux is added, a third fuel type being a coal which may be used when mixed with another coal, and a fourth fuel type being a coal which is not suitable for the gasification.

4. The operating guide system of claim 1, wherein the determining gasification suitability type information comprising:
when the selected fuel includes coal and flux, determining the gasification suitability type information based on a flux input ratio provided by the input.

5. The operating guide system of claim 1, wherein the determining gasification suitability type information:
when the selected fuel includes a primary coal and a secondary coal to be mixed with the primary coal, determining the gasification suitability type information while increasing a mixing ratio of the secondary coal by a predetermined ratio.

6. The operating guide system of claim 1, wherein the one or more programs further include instructions for:
deriving operating conditions information, the derived operating conditions including upper limit and lower limit temperatures of slag and upper limit and lower limit temperatures of gasifier for the selected fuel.

7. The operating guide system of claim 6, wherein the driving operating conditions information comprises:
deriving the upper limit and lower limit temperatures of slag by analyzing a crystal phase and solid-liquid equilibrium temperature of slag of the selected fuel and,
deriving the upper limit and lower limit temperatures of gasifier temperature based on the derived upper limit and lower limit temperatures of slag.

8. The operating guide system of claim 1, wherein the one or more programs further include instructions for:
generating a start-up table comprising a supply fuel input amount and main control factor state values for each step of a start-up process, the start-up process comprising coal burner stages of start, ready, and load up, and
displaying, on the screen, the supply fuel input amount and the main control factor state values for each step of the start-up process.

9. The operating guide system of claim 8, wherein the generating the start-up table comprises:
generating the supply fuel input amount and the main control factor state values for each step of the start-up process in the reverse order of the start-up process based on the supply fuel input amount of 100% load.

10. The operating guide system of claim 1,
wherein the one or more programs further includes instructions for:
generating, when an event for a plant stop occurs, a stop guide information for stopping the plant, the stop guide information including control values requiring a user input for each step of a plurality of stops for the plant stop.

11. An operating guide system of a plant utilizing coal gasification, the operating guide system comprising:
an input interface;
a screen;
a processor; and
a storage, connected with the processor by a bus, storing one or more programs configured to be executed by the processor, the one or more programs including instructions for:
receiving, by the input interface, an input selecting a fuel having basic attributes information and slag attributes information;
determining, before the plant is started, gasification suitability type information of the selected fuel, based on a first comparison between the basic attributes information of the selected fuel and a first predetermined reference value and a second comparison between the slag attributes information of the selected fuel and a second predetermined reference value;
storing the gasification suitability type information;
generating performance analysis information of the plant by analyzing, while the plant is operated using the selected fuel, gasifier performance information and synthesis gas cooler performance information of the plant;
generating an operation guide information indicating operation control values for the operation of the plant based on the generated performance analysis of the plant; and
displaying, on the screen, the operation guide information with the operation control values,
wherein the slag attributes information includes coal conversion temperature (° C.), total slag thickness (mm), liquidus slag thickness (mm), average slag viscosity (poise), and muffle length versus slag thickness {%} of the selected fuel.

12. An operating guide system of a plant utilizing coal gasification, the operating guide system comprising:
an input interface;
a screen;
a processor; and
a storage, connected with the processor by a bus, storing one or more programs configured to be executed by the processor, the one or more programs including instructions for:
receiving, by the input interface, an input selecting a fuel having basic attributes information and slag attributes information;
determining, before the plant is started, gasification suitability type information of the selected fuel, based on a first comparison between the basic attributes information of the selected fuel and a first predetermined reference value and a second comparison between the slag attributes information of the selected fuel and a second predetermined reference value;
storing the gasification suitability type information;
generating performance analysis information of the plant by analyzing, while the plant is operated using the selected fuel, gasifier performance information and synthesis gas cooler performance information of the plant;
generating an operation guide information indicating operation control values for the operation of the plant based on the generated performance analysis of the plant; and
displaying, on the screen, the operation guide information with the operation control values, wherein the determining gasification suitability type information comprises outputting the determined gasification suitability type information into a plurality of fuel types including a first fuel type being a coal which may be used without being added with flux or another coal, a second fuel type being a coal which may be used when the flux is added, a third fuel type being a coal which may be used when mixed with another coal, and a fourth fuel type being a coal which is not suitable for the gasification and then classifying the selected fuel into one of the plurality of fuel types.

* * * * *